(12) United States Patent  (10) Patent No.: US 8,048,106 B2
Widmann  (45) Date of Patent: Nov. 1, 2011

(54) SURGICAL INSTRUMENT (76) Inventor: Heinrich Widmann, Buchheim (DE)

( * ) Notice: Subject to any disclaimer, the term of this patent is extended or adjusted under 35 U.S.C. 154(b) by 394 days.

(21) Appl. No.: 12/225,191

(22) PCT Filed: Mar. 2, 2007

(86) PCT No.: PCT/EP2007/001784
§ 371 (c)(1),
(2), (4) Date: Sep. 16, 2008

(87) PCT Pub. No.: WO2007/107227
PCT Pub. Date: Sep. 27, 2007

(65) Prior Publication Data
US 2009/0209998 A1  Aug. 20, 2009

(30) Foreign Application Priority Data
Mar. 17, 2006 (DE) .......................... 10 2006 012 754

(51) Int. Cl.
A61B 17/00 (2006.01)
(52) U.S. Cl. ......... 606/205; 606/206; 606/207; 606/208
(58) Field of Classification Search .................. 606/167, 606/205–208
See application file for complete search history.

(56) References Cited

U.S. PATENT DOCUMENTS

| 5,451,227 | A | * | 9/1995 | Michaelson | 606/83 |
|---|---|---|---|---|---|
| 5,569,258 | A | * | 10/1996 | Gambale | 606/83 |
| 5,584,844 | A | * | 12/1996 | Weisshaupt | 606/170 |
| 5,961,531 | A | * | 10/1999 | Weber et al. | 606/167 |
| 6,126,674 | A | * | 10/2000 | Janzen | 606/206 |
| 6,214,010 | B1 | * | 4/2001 | Farley et al. | 606/83 |
| 6,520,979 | B1 | * | 2/2003 | Loubens et al. | 606/205 |
| 6,547,805 | B1 | * | 4/2003 | Loubens et al. | 606/206 |
| 6,685,710 | B2 | * | 2/2004 | Agbodoe et al. | 606/83 |
| 6,723,103 | B2 | * | 4/2004 | Edwards | 606/83 |
| 6,802,852 | B2 | * | 10/2004 | Tontarra | 606/208 |
| 6,991,633 | B2 | * | 1/2006 | Agbodoe | 606/83 |
| 7,052,505 | B2 | * | 5/2006 | Widmann | 606/167 |
| 7,377,933 | B2 | * | 5/2008 | Martin | 606/206 |
| 7,611,517 | B2 | * | 11/2009 | Lim | 606/86 A |
| 7,691,107 | B2 | * | 4/2010 | Schneiter | 606/83 |
| 7,708,757 | B2 | * | 5/2010 | Ganter | 606/205 |
| 2002/0147460 | A1 | * | 10/2002 | Bacher | 606/205 |
| 2002/0151931 | A1 | * | 10/2002 | Tontarra | 606/205 |
| 2003/0088268 | A1 | * | 5/2003 | Weinmann | 606/205 |
| 2006/0111737 | A1 | * | 5/2006 | Wenzler et al. | |

OTHER PUBLICATIONS

PCT International Search Report mailed on Oct. 17, 2007 for the corresponding International patent application No. PCT/EP2007/001784 (English translation enclosed).*

* cited by examiner

Primary Examiner — Gary Jackson
Assistant Examiner — Katrina Stransky
(74) Attorney, Agent, or Firm — Posz Law Group, PLC (57) ABSTRACT The invention relates to a surgical instrument comprising a shank and a slide which is mounted so as to be slideable along the shank. At least one guide element guided in at least one longitudinal groove is provided on the shank or the slide. The shank and the slide are each connected to a handle part, one handle part being mobile in relation to the other handle part about a pivot and being provided with a slot in which a cross bracket of the slide engages. The invention is characterized in that the position of the handle part in relation to the other handle part can be altered in the region of the pivot.

25 Claims, 6 Drawing Sheets

SURGICAL INSTRUMENT

CROSS REFERENCE TO RELATED APPLICATIONS

This application is a U.S. national stage application of PCT/EP2007/001784 filed on Mar. 2, 2007, and claims priority to, and incorporates by reference, German Patent Application No. DE 10 2006 012 754.4 filed on Mar. 17, 2006.

The invention relates to a surgical instrument with a shank, and with a slide which is mounted so as to be slideable along the shank, at least one guide element guided in at least one longitudinal groove being provided on the shank or the slide, and the shank and the slide each being connected to a handle part, of which one handle part is movable in relation to the other handle part about a pivot and is provided with a slot in which a crosspiece of the slide engages.

PRIOR ART

Instruments of this kind are designated as sliding shaft instruments. They are used to carry out cutting, shearing, clamping or similar operations, for example in the human body. In these operations, the slide is moved along a slide surface of the shank by actuation of the handle parts, and a working element is actuated at the end thereof.

Sliding shaft instruments of this kind are used in particular as bone punches, as ear forceps, and in gynecological biopsies. A general problem is that surgical instruments of this kind are products which have a very wide variety of hinges, guides or grooves and channels. Such instruments are therefore extremely difficult to clean and sterilize, but cleaning of surgical instruments is of course of the utmost importance. The hygiene requirements for such surgical instruments are greatly increased due to the risk of transmission of diseases, for example hepatitis or AIDS.

An instrument of the abovementioned type is known from DE 201 03 630, for example.

OBJECT

The object of the present invention is to further improve and simplify an instrument of the abovementioned type.

SOLUTION

The object is achieved by virtue of the fact that the position of the handle part in relation to the other handle part can be altered in the area of the pivot.

This change of position has the effect that the cross-piece is released, such that the slide can be moved freely along the shank, and the corresponding guide elements can be released. If this instrument is then to be brought back to the position of use, the two bores, through which a rotary element passes, are brought back into coincidence, such that only a rotation of the two handle parts relative to each other is possible.

The change of position is brought about by a locking mechanism which, on the one hand, permits a rotation of the two handle parts relative to each other but, on the other hand, also permits the possibility of changing the position of one handle part. This is achieved, for example, by a transverse pin that has a different diameter. Moreover, the bore in the handle part whose position is to be changed should be adjoined by an oblong hole that has a smaller width than the actual pivot bore. Those parts of the pin with the greater diameter can be fitted in the bores for rotating the handle parts. However, when the stepped pin is displaced, a pin part of smaller diameter can pass into the area of the oblong hole, such that the latter can be moved along the pin part of smaller diameter.

A further concept of the present invention is that the movement of the slide along the shank can be limited by a locking mechanism. When this locking is canceled, the slide and the shank should be separable from each other like scissors about a pivot.

In one illustrative embodiment, the pivot is situated between the shank and a fixed handle part, while in a second illustrative embodiment the pivot is situated between the slide and a movable handle part.

It is also conceivable for the slide to be assigned a pusher part, in which case the pusher part is coupled, on the one hand, to the movable handle part and, on the other hand, to the slide via the pivot. It is intended here that the pusher part be connected to the fixed handle part, while the slide is released by actuation of the locking mechanism. In a preferred illustrative embodiment, however, it should also be possible, after actuation of the locking mechanism, to perform a further movement of the slide or pusher part in order to release it from the shank, in which case the guide elements can each be guided out of the corresponding longitudinal grooves.

Depending on the illustrative embodiment, the guide elements or longitudinal grooves can be located on or in the slide. As regards the locking mechanisms too, there are a number of possibilities, as described in the dependent claims. A locking mechanism is particularly preferred which engages behind the movable handle part and is movable as a rocker lever in a corresponding recess in the fixed handle part. If the limit stop has a stepped design, or if a limit stop edge of the rocker lever on which the movable handle part acts has a stepped design, the opening width of the two handle parts relative to each other can be varied, which greatly varies the possibility of separation of slide and shank.

DESCRIPTION OF THE FIGURES

Further advantages, features and details of the invention will become evident from the following description of preferred illustrative embodiments and by reference to the drawing, in which.

Figure 1:
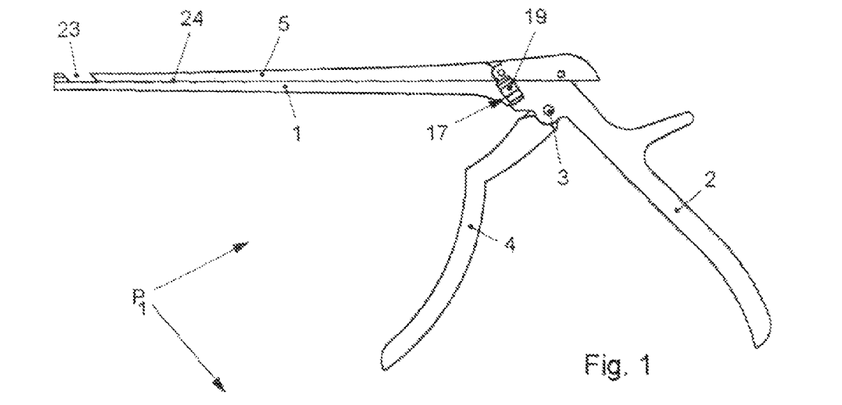
FIG. 1 shows a plan view of a surgical instrument according to the invention.
Figure 2:
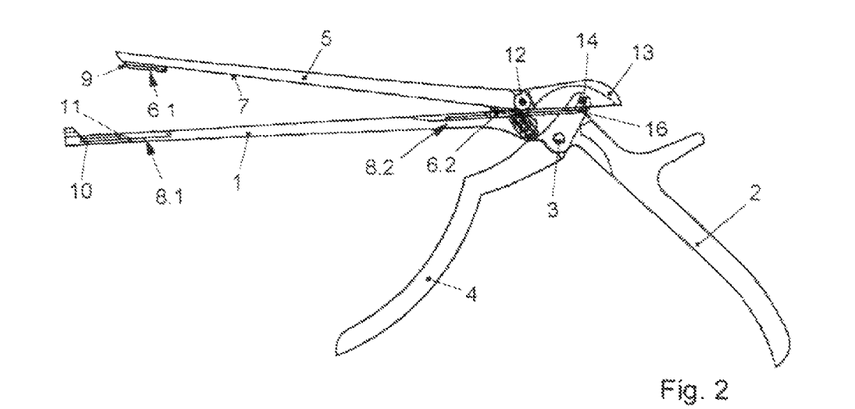
FIG. 2 shows a plan view of the surgical instrument according to FIG. 1 in a further position of use.
Figure 3:
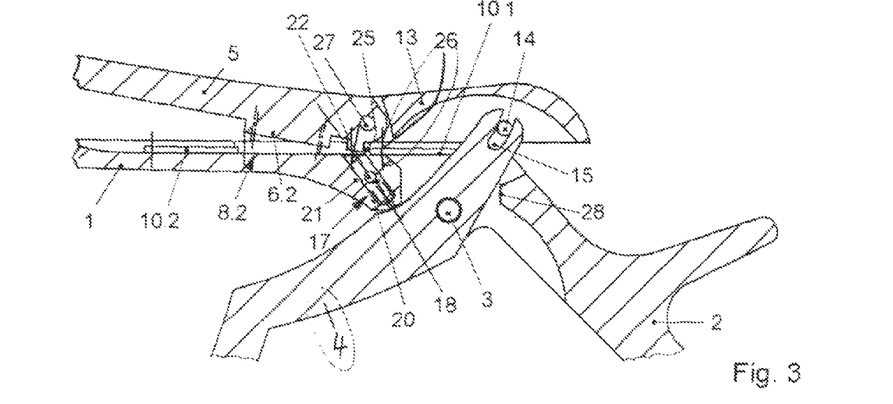
FIG. 3 shows an enlarged sectional view of part of the surgical instrument according to FIG. 2.

According to FIGS. 1 and 2, a surgical instrument $P_1$ according to the invention has a shank 1, which is connected to a fixed handle part 2. This fixed handle part 2 is also connected via a pivot 3 to a movable handle part 4, this movable handle part 4 being able to be swiveled about the pivot 3. By the movement of the movable handle part 4, a slide 5 is moved along the shank 1. Guide elements 6.1 and 6.2, which are provided on an underside 7 of the slide 5, engage in longitudinal grooves 8.1 and 8.2 in the shank 1, said guide elements 6.1 and 6.2 being configured in an inverted P shape, such that lateral rails 9 on the guide elements 6.1 and 6.2 can be guided in undercut grooves 10 and 10.2 in the longitudinal grooves 8.1 and 8.2. Partial areas 11 of these longitudinal grooves 8.1 and 8.2 are, however, provided with small undercut grooves 10 and 10.2, such that the guide element 6.1 or 6.2 can be lifted out of these partial areas 11. In this case, the shank 1 and slide 5 execute a forceps-like movement relative to each other, the slide 5 turning about a pivot 12. By way of this pivot 12, the slide 5 is connected to a pusher part 13 which is provided below a crosspiece 14, which engages in a slot 15 (see FIG. 3) in the movable handle part 4, with guide elements 16, which in turn are guided in undercut grooves 10.1 in a continuation of the longitudinal groove 8.2.

To limit the movement of the slide 5 relative to the shank 1, a locking mechanism 17 is provided as described in DE 201 03 630 A1. This locking mechanism 17 comprises a pin as limit stop 18 which, by actuation by means of a slide button 19, can be pushed out of the longitudinal groove 8.2 counter to the force of a helical spring (not shown) located in a cavity 20 of a blind hole 21. Between the slide button 19 and the limit stop 18, there is a connecting pin 22.

The mode of operation of the present invention is as follows:

In the position of use, the guide elements 6.1, 6.2 and 16 are in engagement with the corresponding undercut grooves 10, 10.1 and 10.2, such that, when the movable handle part 4 is actuated, the slide 5 can be moved along the shank 1, and a sample of tissue is removed, for example by means of a punch jaw 23.

If the instrument is to be cleaned, for example, this applies especially to the space 24 between the shank 1 and the slide 5, since blood or tissue fluid can gather in this space 24. To make this cleaning easier, it is advisable to separate the slide 5 from the shank 1. This is done by the locking mechanism 17 being actuated, i.e. the limit stop 18 being moved downward in the blind hole 21 by actuation of the slide button 19, such that the limit stop 18 is driven out of the inside width of the longitudinal groove 8.2. In this way, the slide 5 and also the pusher part 13 can be moved further to the right, such that the guide elements 6.1 and 6.2 move into an area of the longitudinal grooves 8.1 and 8.2 in which they are no longer trapped in undercut grooves 10 and 10.2, respectively. A rear edge 25 of the guide element 6.2 strikes a control edge 26 in the longitudinal groove 8.2, such that the slide 5 is turned about the pivot 12, and here in particular about a transverse pin 27. In this way, the slide 5 is lifted from the shank 1. This opening is generally enough to permit adequate cleaning of the instrument.

However, if the slide 5 is to be removed from the shank 1 completely, the movable handle part 4 can be opened still further about the pivot 3, such that the guide elements 16 of the pusher part 13 are in the end also disengaged from the undercut grooves 10.1. In this way, the pusher part 13 can also be detached from the fixed handle part 2, the crosspiece 14 sliding out of the slot 15.

If the removal of the slide 5 and pusher part 13 from the shank 1 and fixed handle part 2, respectively, is to be prevented, the fixed handle part 2 can be provided, near the movable handle part 4, with a limit stop 28 which ensures that the movable handle part 4 cannot be opened so far that the guide elements 16 are disengaged from the undercut grooves 10.1.

During assembly, it suffices to press the slide 5 and the shank 1 together such that the guide element 6.2 presses the limit stop 18 downward in the blind hole 21. If the movable handle part 4 is now actuated, the slide 5 is moved forward via the pusher part 13, the guide element 6.2 moving across the limit stop 18, which then travels into the inside width of the longitudinal groove 8.2 under the pressure of the helical spring. At this instant, however, the guide elements 6.1 and 6.2 are already trapped by the undercut grooves 10 and 10.2, such that the slide 5 cannot be lifted from the shank 1.

If the pusher part 13 together with the slide 5 has been removed from the shank 1 and fixed handle part 2, then of course the guide elements 16 have to be fitted into the undercut grooves 10.1 before the slide 5 and shank 1 are pressed together.

Figure 4:
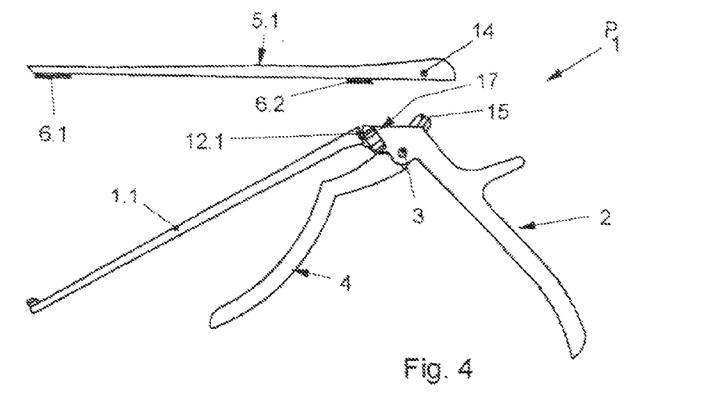
FIG. 4 shows a plan view of a further illustrative embodiment of a surgical instrument in an exploded illustration.

FIG. 4 shows a further illustrative embodiment of a surgical instrument $P_1$. The fixed handle part 2 and the movable handle part 4 correspond to those according to FIGS. 1 and 2, as also do the pivot 3, the locking mechanism 17, the crosspiece 14 and the slot 15. The guide elements 6.1 and 6.2 are likewise provided on the slide 5.1, which in this case has no pivot, and in which instead the pusher part forms part of the overall slide 5.1.

The difference, however, is that the shank 1.1 is not integrally connected to the fixed handle part 2, but is instead articulated thereon via a pivot 12.1. The rear guide element 16 is also absent, with the result that, after the locking mechanism 17 has been actuated and the shank 1.1 folded down, the slide 5.1 comes completely free from the shank 1.1 and the fixed handle part 2.

Figure 5:
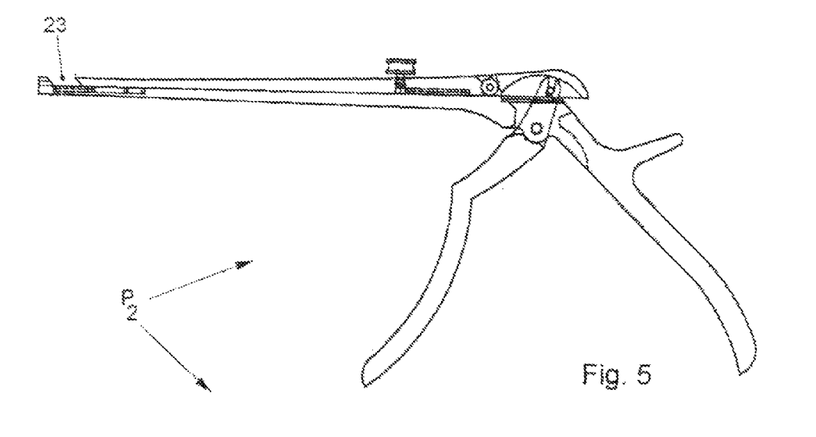
FIG. 5 shows a plan view of a further illustrative embodiment of a surgical instrument.
Figure 6:
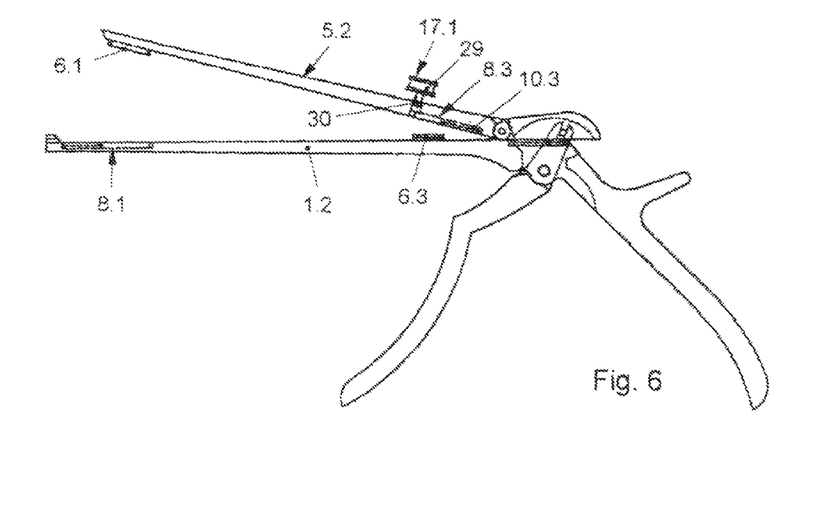
FIG. 6 shows a plan view of the surgical instrument according to FIG. 5 in a further position of use.
Figure 7:
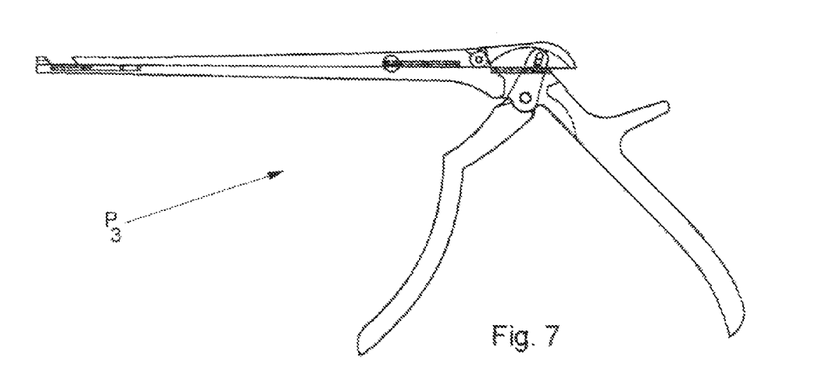
FIG. 7 shows a plan view of a further illustrative embodiment of a surgical instrument.

The illustrative embodiment of a surgical instrument $P_2$ according to FIGS. 5 and 6 differs from the above-described illustrative embodiments in terms of the design of the locking mechanism and the arrangement of the guide elements and longitudinal grooves. Whereas in the front area, near the punch jaw 23, the guide element 6.1 protrudes as before from the slide 5.2 and engages in the longitudinal groove 8.1 in the shank 1.2, a guide element 6.3 in the proximal area protrudes from the shank 1.2 and cooperates with a longitudinal groove 8.3 in the slide 5.2. In this case, the corresponding undercut grooves 10.3 in the longitudinal groove 8.3 are also provided behind the guide element 6.3. By contrast, the locking mechanism 17.1 is located in front of the guide element 6.3. This locking mechanism 17.1 has a pull knob 29, with which a limit stop designed as a pin 30 can be pulled from the inside width of the longitudinal groove 8.3. In this way, the slide 5.2 can be moved further to the left, such that the guide element 6.3 moves into an area of the longitudinal groove 8.3 that is no longer covered by the undercut groove 10.3. In this way, the guide element 6.3 frees the slide 5.2, such that the latter can fold out, since the guide element 6.1 in the longitudinal groove 8.1 is also freed at the same time.

Figures 8, 9, 10:
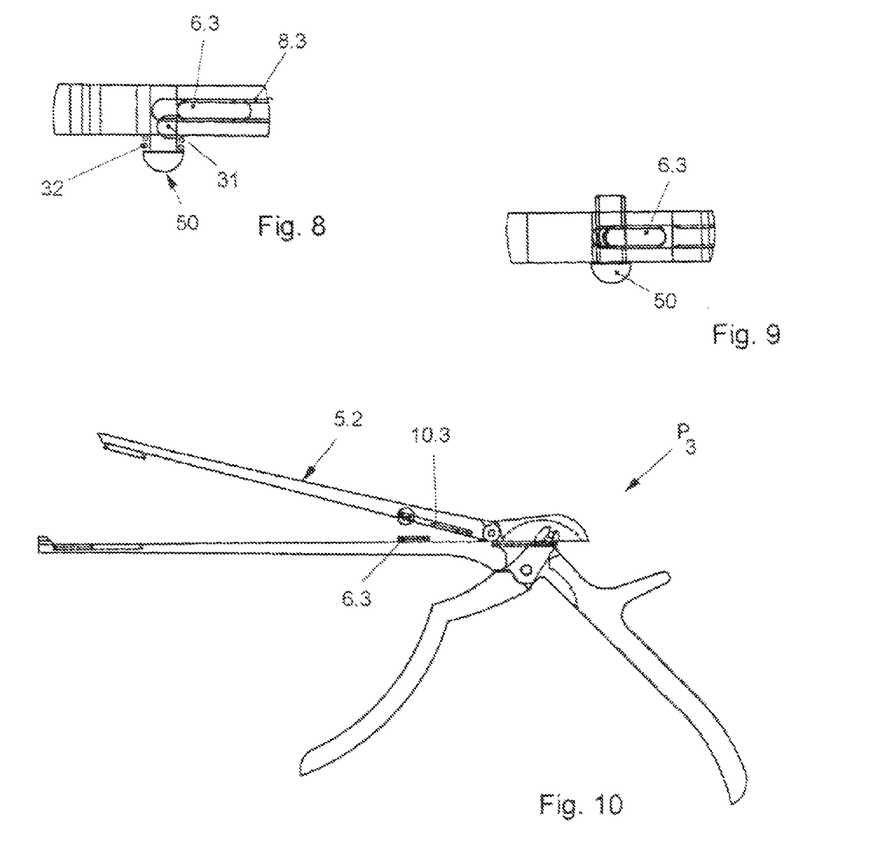
FIG. 8 shows an enlarged bottom view of part of a slide from FIG. 7.
FIG. 9 shows an enlarged bottom view of part of the slide according to FIG. 7 in a further position of use.
FIG. 10 shows a plan view of the surgical instrument according to FIG. 7 in a further position of use.

The illustrative embodiment of a surgical instrument $P_3$ according to the invention, shown in FIGS. 7 to 10, differs from those described above likewise in terms of the design of the locking mechanism. It is similar in principle to the illustrative embodiment according to FIGS. 5 and 6, except for a limit stop, designed as a pushbutton 50, which is arranged laterally on the slide 5.2 and in which a recess 31 is formed. When the pushbutton 50 is pressed counter to the force of a spring 32, the recess 31 comes into line with the longitudinal groove 8.3, such that the guide element 6.3, as is shown in FIG. 9, can travel into the recess 31, with the result that it slides out of the undercut grooves 10.3 and the slide 5.2 is freed.

Figure 11:
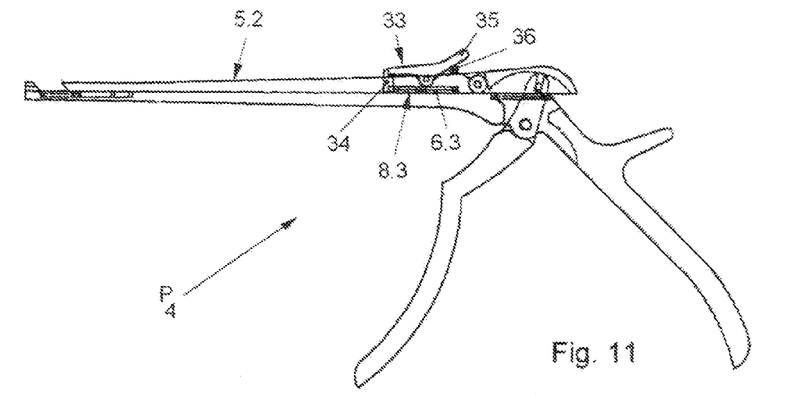
FIG. 11 shows a plan view of a further illustrative embodiment of a surgical instrument.

In the illustrative embodiment of a surgical instrument $P_4$ according to FIG. 11, a rocker lever 33 sits on the slide 5.2 and comprises, projecting down from it, a lug 34 which acts as a limit stop and which engages in the inside width of the longitudinal groove 8.3 in front of the guide element 6.3. When the rocker lever 33 is actuated by pressing on the lever arm 35 counter to the force of a spring 36, the lug 34 is removed from the inside width of the longitudinal groove 8.3, such that the guide element 6.3 can reach an area in the longitudinal groove 8.3 in which it is freed.

Figure 12:
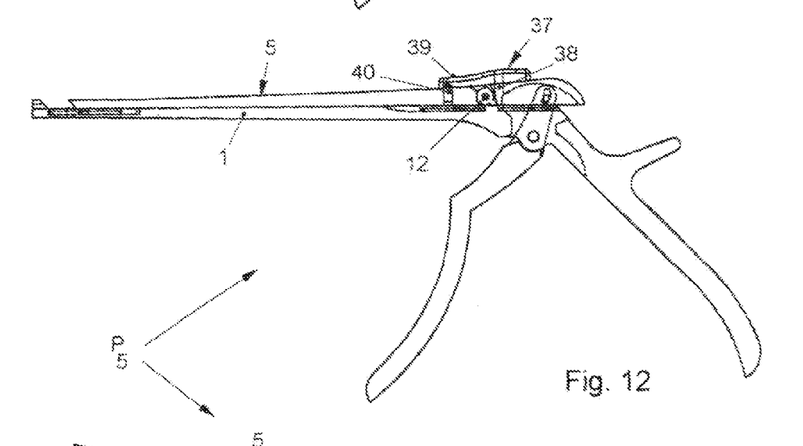
FIG. 12 shows a plan view of a further illustrative embodiment of a surgical instrument.
Figure 13:
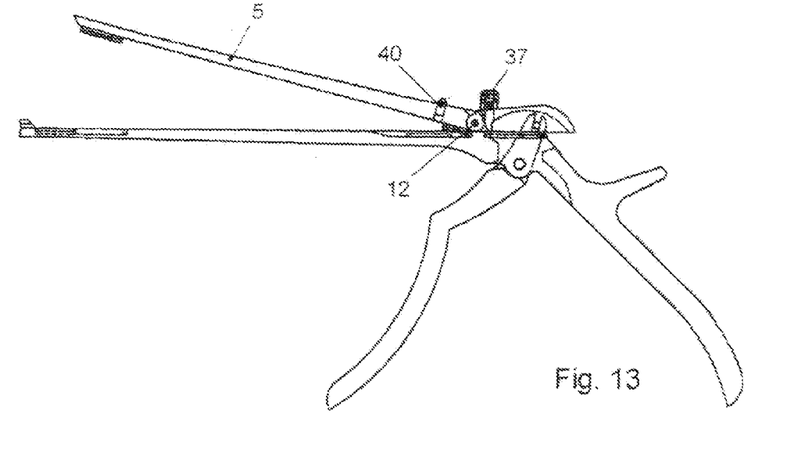
FIG. 13 shows a plan view of the surgical instrument according to FIG. 12 in a further position of use.

In the illustrative embodiment of a surgical instrument $P_5$ according to FIGS. 12 and 13, a rotary lever 37 is located on the slide 5. The rotary lever 37 can be turned about a rotation axis 38, said rotation axis 38 being situated behind the pivot 12. In the position of use shown in FIG. 12, the rotary lever 37 engages with a front pressure arm 39 over the slide 5, such that the slide 5 is held bearing on the shank 1. This position is secured by a spring-mounted locking pin 40 in the slide 5.

When the rotary lever 37 is turned through 90°, as shown in FIG. 13, the pressure arm 39 is also removed from the slide 5, such that the slide 5 can fold open about the pivot 12.

Figure 14:
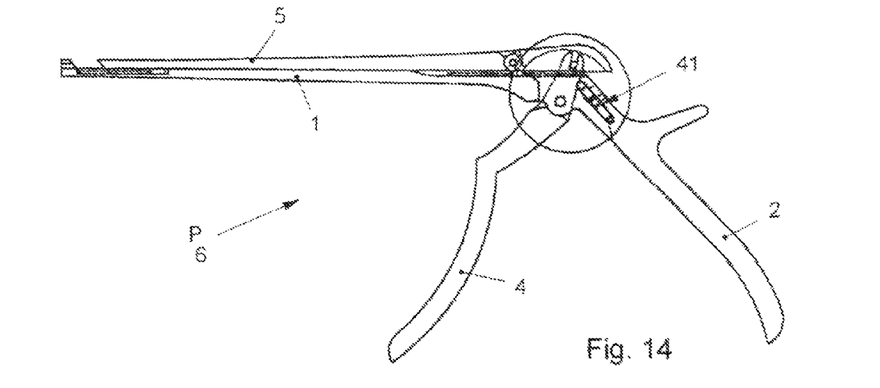
FIG. 14 shows a plan view of a further illustrative embodiment of a surgical instrument.

In another and also very much preferred illustrative embodiment of a surgical instrument $P_6$ according to FIGS. 14 to 17, a rocker lever 41 is situated in the fixed handle part 2 and can act as a limit stop for the movable handle part 4. This rocker lever 41 can turn about an axis 42, such that its upper edge 43 either engages behind the movable handle part 4 or frees it. Three positions are possible. According to FIG. 16, the edge 43 is recessed in the fixed handle part 2 and, as is shown in FIG. 14, engages behind the upper part of the movable handle part 4. At this instant, the guide element 6.2 cannot escape from the undercut grooves 10.2 and is instead trapped in these grooves 10.2, such that the slide 5 cannot be separated from the shank 1.

Figure 15:
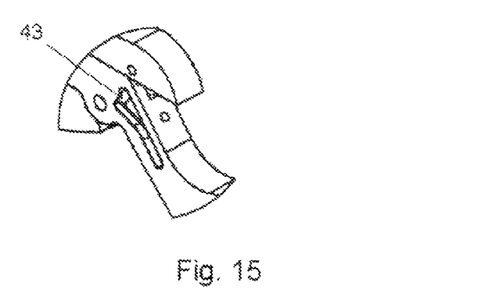
FIGS. 15 and 16 show enlarged perspective views of a detail from FIG. 14 in different positions of a rocker lever.
Figure 16:
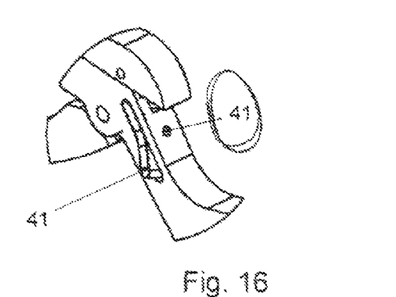
Figure 17:
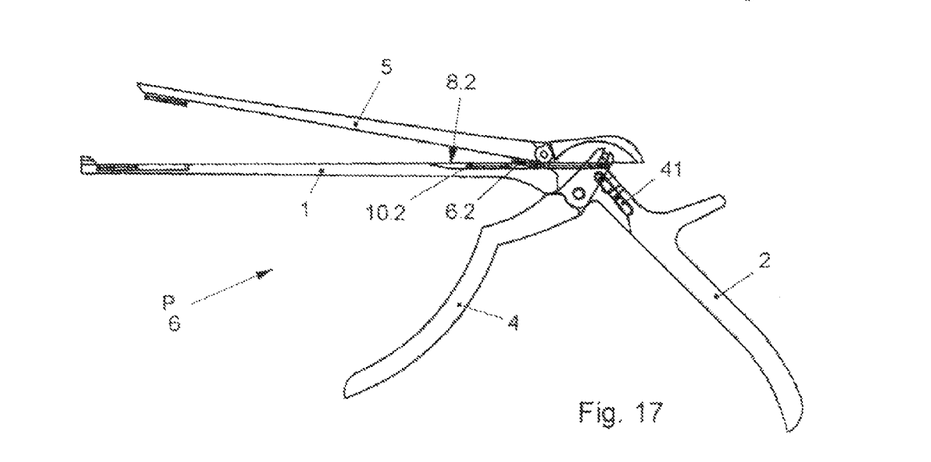
FIG. 17 shows a plan view of the surgical instrument according to FIG. 14 in a further position of use.

If the rocker lever 41 is now actuated and assumes a position as shown in FIG. 15, the upper part of the movable handle part 4 is freed, as is indicated in FIG. 17, such that the guide element 6.2 can also move into an area of the longitudinal groove 8.2 in which it is no longer trapped by the undercut grooves 10.2.

By means of a stepped formation of the edge 43, a third position is also conceivable in which the movable handle part 4 can be opened still further, such that the guide element 16 can be removed from the undercut grooves 10.2 and the slide 5 is completely freed.

Figures 18, 19, 21:
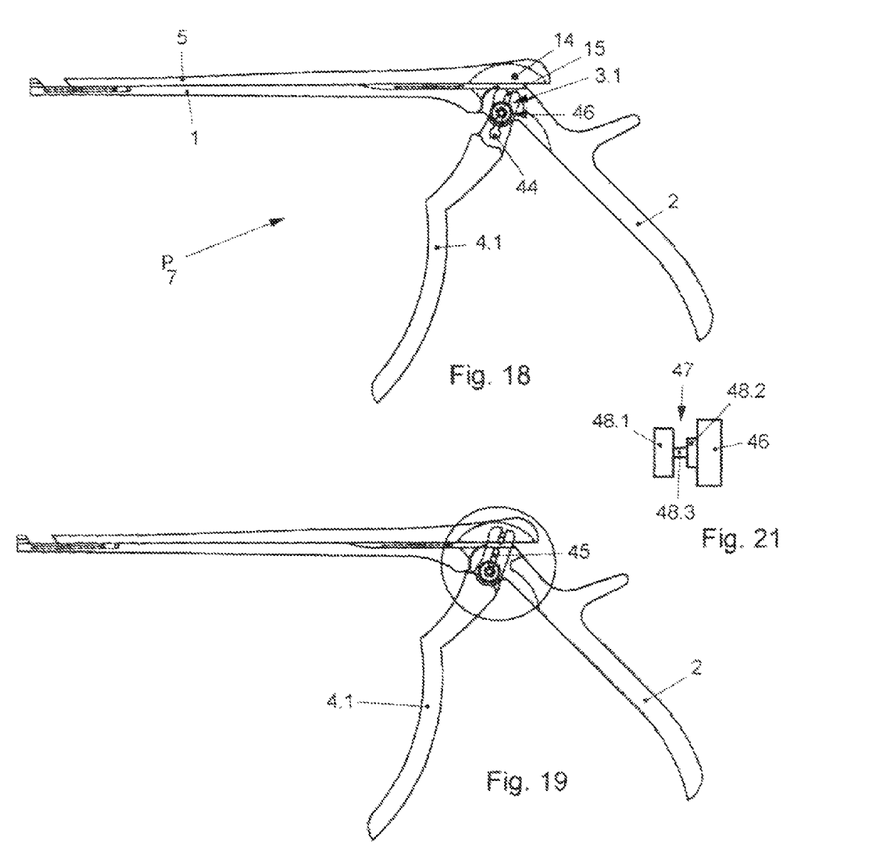
FIG. 18 shows a plan view of a further illustrative embodiment of a surgical instrument during assembly.
FIGS. 19 and 20 show two plan views of the surgical instrument according to FIG. 18 in different positions of use.
FIG. 21 shows a plan view of a pushbutton, shown enlarged, with a protruding stepped pin.
Figure 20:
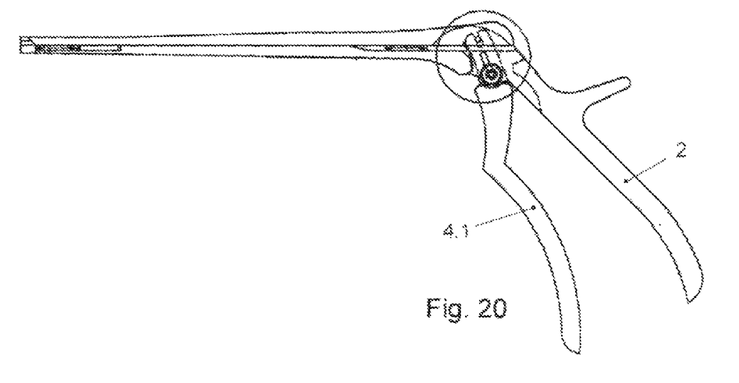

A particularly simple illustrative embodiment of a surgical instrument $P_7$ is shown in FIGS. 18 to 20. There, the pivot 3.1 is designed in a particularly simple way, such that protection is requested for this especially. In addition to a bore 44 being formed in the upper area of the movable handle part 4.1 and corresponding to a bore (not shown) in the fixed handle part 2, this bore 44 is also adjoined by an oblong hole 45. This embodiment is assigned a special pushbutton 46, from which there protrudes a stepped pin 47 (shown enlarged in FIG. 21).

The pushbutton 46 with its pin 47 is subjected to the pressure of a suitably arranged helical spring. In the normal position, the pin parts 48.1 and 48.2 of greater diameter are situated in the bores 44 of the movable handle part 4.1 and of the fixed handle part 2. When, by moving this arrangement however, the pin part 48.3 of smaller diameter, corresponding to the width of the oblong hole 45, is brought into the area of the latter, the movable handle part 4.1, as shown in FIG. 18, can be pulled downward. By this means, the crosspiece 14 slips out of the slot 15 and the slide 5 is freed, such that it can be detached from the shank 1.

In this illustrative embodiment, the fixed handle part 2 also comprises a leaf spring 49, which counteracts a rotation movement of the movable handle part 4. In this way, the manufacturer does not have to provide a corresponding spreader element between the fixed handle part 2 and the movable handle part 4.

LIST OF REFERENCE SIGNS 1 shank
2 fixed handle part
3 pivot
4 movable handle part
5 slide
6 guide element
7 underside
8 longitudinal groove
9 rail
10 undercut groove
11 partial area
12 pivot
13 pusher part
14 crosspiece
15 slot
16 guide element
17 locking mechanism
18 limit stop
19 slide button
20 cavity
21 blind hole
22 connecting pin
23 punch jaw
24 space
25 rear edge
26 control edge
27 transverse pin
28 limit stop
29 pull knob
30 pin
31 recess
32 spring
33 rocker lever
34 lug
35 lever arm
36 spring
37 rotary lever
38 rotation axis
39 pressure arm
40 locking pin
41 rocker lever
42 axis
43 edge
44 bore
45 oblong hole
46 pushbutton
47 pin
48 pin parts
49 leaf spring
50 pushbutton
P surgical instrument

The invention claimed is:

1. A surgical instrument comprising: a shank being connected to a fixed handle part at a first pivot;
   a pusher part having a crosspiece;
   a slide, connected to the pusher part at the first pivot, and mounted so as to be slideable along the shank in a manner limited by a locking mechanism;
   at least one guide element guided in at least one longitudinal groove being provided in the shank or the slide; and
   a movable handle part that is movable in relation to the fixed handle part about a second pivot, wherein the movable handle is provided with a slot in which the crosspiece of the pusher part engages, the pusher part being guided longitudinally by the shank and being slideable in line with the slide along the shank, and
   the slide and the shank can be separated from each other in a scissor movement of the slide about the first pivot connecting the slide and the pusher part after a locking of the locking mechanism is canceled.

2. The surgical instrument as claimed in claim 1, wherein the guide element has a rear edge and the longitudinal groove has a control edge, and
   the pusher part can be moved further towards the fixed handle part along the shank after the locking of the locking mechanism has been canceled, so that the rear edge of the guide element strikes the control edge in the longitudinal groove, and so that the slide and the shank are separated from each other in a scissor movement of the slide about the pivot connecting the slide and the pusher part.

3. The surgical instrument as claimed in claim 1, wherein the first pivot connecting the slide to the pusher part is composed of a transverse pin by means of which tongues engaging in one another like a fork are connected to one another.

4. The surgical instrument as claimed in claim 1, wherein a limit stop can be moved behind or in front of the guide element in and out of the inside width of at least a part of the longitudinal groove.

5. The surgical instrument as claimed in claim 4, wherein the limit stop is guided in a blind hole arranged in the shank or slide.

6. The surgical instrument as claimed in claim 4, wherein the limit stop is guided obliquely with respect to the longitudinal groove.

7. The surgical instrument as claimed in claim 4, wherein the limit stop bears against an energy-accumulating means.

8. The surgical instrument as claimed in claim 7, wherein the energy-accumulating means is a helical spring.

9. The surgical instrument as claimed in claim 4, wherein the limit stop is connected via a connecting pin to a slide button situated on the outside of the shank.

10. The surgical instrument as claimed in claim 9, wherein the connecting pin has a threaded portion with which the connecting pin can be fitted into a threaded bore in the limit stop.

11. The surgical instrument as claimed in claim 4, wherein the limit stop is connected to a pull knob on an outside of the slide.

12. The surgical instrument as claimed in claim 4, wherein a recess, formed in the limit stop, constitutes a continuation of the longitudinal groove when the limit stop is displaced.

13. The surgical instrument as claimed in claim 4, wherein the limit stop is connected to a rocker lever arranged on the slide.

14. The surgical instrument as claimed in claim 4, wherein the limit stop is connected to a rotary lever arranged on the slide.

15. The surgical instrument as claimed in claim 1, wherein a movement of the movable handle part is limited by a limit stop.

16. The surgical instrument as claimed in claim 15, wherein the limit stop is a rocker lever.

17. The surgical instrument as claimed in claim 15, wherein the limit stop permits at least two opening positions of the movable handle part.

18. The surgical instrument as claimed in claim 15, wherein the limit stop in the fixed handle part is arranged behind the movable handle part and is pivotable about an axis.

19. The surgical instrument as claimed in claim 1, wherein the second pivot connecting the two handle parts to each other has a pushbutton from which there protrudes a pin of stepped diameter.

20. The surgical instrument as claimed in claim 19, wherein the pin of stepped diameter passes through two congruent bores arranged in the handle parts, and wherein the bore in the movable handle part is adjoined by a recess.

21. The surgical instrument as claimed in claim 20, wherein the recess has a width that corresponds to a diameter of lesser extent on the pin.

22. The surgical instrument as claimed in claim 15, wherein the limit stop permits three opening positions of the movable handle part.

23. The surgical instrument as claimed in claim 19, wherein the pin of the stepped diameter passes through two congruent bores arranged in the handle parts, and wherein the bore in the movable handle part is adjoined by an oblong hole.

24. A surgical instrument comprising: a shank directly connected to a fixed handle part about a first pivot;
   a slide, connected to a movable handle part, that is mounted so as to be slideable along the shank and the fixed handle part in a manner limited by a locking mechanism; and
   at least one guide element guided in at least one longitudinal groove being provided in the shank and in the fixed handle part or the slide, wherein
   the movable handle part is movable in relation to the fixed handle part about a second pivot, and is provided with a slot in which a cross-piece of the slide engages,
   the slide and the shank can be separated from each other in a scissor movement of the shank about the first pivot connecting the shank and the fixed handle part, after a locking of the locking mechanism has been canceled, while the slide stays connected to the fixed handle part.

25. The surgical instrument as claimed in claim 24, wherein the first pivot connecting the shank to the fixed handle part is composed of a transverse pin by means of which tongues engaging in one another like a fork ore connected to one another.

* * * * *